US006241689B1

(12) United States Patent
Chard et al.

(10) Patent No.: US 6,241,689 B1
(45) Date of Patent: Jun. 5, 2001

(54) DIAGNOSTIC TEST APPARATUS

(75) Inventors: Michael John Chard, Flintshire; Philip Robert Goodwin, Chester; Christopher John Smith, Clwyd; Robert Woolston, Hertfordshire; Bernard Sams, London, all of (GB)

(73) Assignee: Provalis UK Limited (GB)

(*) Notice: Subject to any disclaimer, the term of this patent is extended or adjusted under 35 U.S.C. 154(b) by 0 days.

(21) Appl. No.: 09/076,825

(22) Filed: May 13, 1998

Related U.S. Application Data

(63) Continuation of application No. PCT/GB96/02751, filed on Nov. 13, 1996.

(30) Foreign Application Priority Data

Nov. 13, 1995 (GB) .................................................. 9523163
Nov. 14, 1995 (GB) .................................................. 9523288

(51) Int. Cl.[7] ........................................................ A61B 5/00
(52) U.S. Cl. ............................................................ 600/584
(58) Field of Search .................................... 600/573, 578, 600/584; 604/51, 52

(56) References Cited

U.S. PATENT DOCUMENTS

| | | | | |
|---|---|---|---|---|
| 3,252,331 | | 5/1966 | Lancaster et al. . | |
| 4,116,637 | | 9/1978 | Kitahara . | |
| 5,048,539 | * | 9/1991 | Schindele | 600/584 |
| 5,204,063 | | 4/1993 | Allen . | |
| 5,281,208 | * | 1/1994 | Thompson et al. | 604/378 |
| 5,339,829 | | 8/1994 | Thieme et al. . | |
| 5,609,160 | * | 3/1997 | Bahl et al. | 600/584 |
| 5,638,828 | * | 6/1997 | Lauks et al. | 600/573 |

FOREIGN PATENT DOCUMENTS

| | | |
|---|---|---|
| 0 366 241 A2 | 5/1990 | (EP) . |
| 0 635 710 A2 | 1/1995 | (EP) . |
| WO 94/22011 | 9/1994 | (WO) . |

* cited by examiner

*Primary Examiner*—Max Hindenburg
(74) *Attorney, Agent, or Firm*—Pennie & Edmonds LLP

(57) ABSTRACT

Sample collection apparatus is provided which allows for fast, accurate, repeatable sample collection, particularly of blood and saliva samples. This apparatus is adapted to interconnect with a device designed to carry out analyte detection. Kits comprising the sample collection apparatus are also provided.

26 Claims, 3 Drawing Sheets

DIAGNOSTIC TEST APPARATUS

CROSS-REFERENCE TO RELATED APPLICATION

This application is a continuation of PCT/GB96/02751 filed Nov. 13, 1996.

BACKGROUND OF THE INVENTION

The present invention relates to apparatus for use in collecting liquid samples, in particular biological samples, e.g. blood or saliva. Such apparatus is useful in collecting samples for use in diagnostic tests, and the invention also provides a kit for use in such tests.

Increasingly, use is being made of rapid diagnostic tests, both for use at home by a patient or for use by doctors in their surgeries. These tests have been made available through the use of diagnostic test devices and/or kits which provide everything needed to collect a sample and to perform the diagnostic test thereon. This enables many such tests to be performed more rapidly with less fuss and inconvenience. One example of such a test is the HELISAL™ test used to diagnose infection by *H. pylori* using a sample of blood.

Of course, such tests, and the test devices/kits provided to perform them, must be capable of providing the required level of accuracy that hospital laboratories can achieve, or at least a level of accuracy approaching that of hospital laboratories. In addition, it is often the case that the sample size required for the test fall within a particular range. For home use, and even for use by a doctor in the surgery, accurate measurement of sample volume may present problems. In addition, handling of samples which may represent a "biohazard" can be difficult. Thus, what is required is some form of apparatus which will allow collection of a sample in the right volume range, while at the same time minimising the risk of contact with the sample by the user.

In general, at present, samples are first collected and then transferred to a means, be it a device or the like or a simple test strip, where the test is performed. For example, to perform a test on a sample of blood, the person performing the test might prick the subject's finger and then use a simple capillary to draw up a sample of blood. This sample would then be transferred to the device or test strip for the reaction to occur. Clearly, it would be better if one could provide a sample collection apparatus which would accurately take up a "fixed" volume of sample and which would then release the sample in such a way that the sample is made available accurately and quickly every time, thus ensuring accurate and repeatable results.

SUMMARY OF THE INVENTION

We have now devised such an apparatus. This is simple to use, can be adapted easily to collect different types of sample as well as different sample sizes and which also minimises the risk of user contact with the sample, particularly when transferring the sample to a device designed to perform a diagnostic test on the sample. In particular, the apparatus is designed to connect with a device or housing which incorporates an analyte detection means. The connection of the two parts ensures that the sample is accurately presented each time a test is performed such that the sample can be quickly and accurately transferred to the detection means.

Thus, in a first aspect, the present invention provides sample collection apparatus adapted to interconnect with a device or housing which incorporates analyte detection means, wherein upon interconnection with said device or housing the sample is presented such that at least a part of any sample in the apparatus will be transferred to the device or housing from the apparatus. Suitably, the apparatus comprises a first portion adapted to be held by the user while collecting the sample, and a second portion comprising sample collection means.

The apparatus could be designed to simply be pushed together with the device or housing incorporating the analyte detection means. However, in one embodiment, the apparatus further comprises alignment means adapted to ensure correct presentation of the sample collection apparatus upon interconnection with the device or housing. One example of such alignment means would be guide rails, or projections designed to align with recesses formed in the device or housing. Furthermore, the alignment means could itself act as interconnection means.

In one preferred embodiment, which is particularly suited to collecting blood samples, the sample collection means comprises at least two members adapted to receive a sample volume therebetween upon bringing the members into contact with a liquid. In particular, the apparatus will work by taking up the sample by capillary action, simply by bringing the members into contact with the sample. Preferably, the members are elongate and could, for instance, be formed by plates, or could form a comb arrangement. In another arrangement there could be provided a two-dimensional arrangement of members with spaces therebetween. The apparatus can easily be adapted to collect particular volumes of sample, simply by means of altering the volume of the spaces between the members. Preferred embodiments include four, five or six elongate members in a comb arrangement providing three, four or five spaces therebetween, respectively, to receive the sample volume.

The exact nature and arrangement of the members is not critical. However, clearly, one would not construct the members of a hydrophilic material. Also, the spacing between the members should be such that the sample will be taken up and held between the members. If the spacing is too great, this will not occur. The essential feature which the arrangement must possess is the ability to both present the liquid sample accurately and allow it to be released quickly and reliably. One example of how this can be achieved would be by having an arrangement of the collection means such that contact over a substantial proportion of its surface area with part of the device or housing was achieved upon interconnection. For example, one arrangement would provide for contact of the sample collection means with a test strip, usually formed of porous material, or with an intermediate member, formed of porous material and designed to take up the sample and transfer it to where the reaction is to be performed, upon interconnection.

It may also be advantageous to coat the sample collector with a substance such as heparin to reduce or eliminate blood clotting.

In an alternative preferred embodiment, which would be particularly suited to collecting saliva samples, the sample collection means is formed from a body of absorbent material. An example of a suitable material is absorbent material comprising one or more sintered polymers. Useful polymers include plastics, such as sintered polyethylene (PE).

This material is bio-compatible, does not fragment, break, deform, etc., and is also able rapidly and consistently to absorb liquid. In addition, it has a controlled pore size, and in this way the material can be formed such that it will readily transfer/give up absorbed material to "downstream"

components in any diagnostic kit. Pore size can be controlled in a number of ways. Firstly, polymer powders of different mean particle sizes can be used. If a polymer powder is not available which has exactly the required pore size, then a powder with a larger mean pore size can simply be ground to the desired particle size. Polymer powders having a mean particle size within the range 20–500 microns are particularly useful.

Another way of controlling particle size is by adjustment of the packing of the polymer powders in the mould before sintering. However, using this method, it is only possible to alter pore size to a smaller degree.

To ensure good uptake of a hydrophilic liquid like saliva, relatively hydrophilic polymers can be used. However, relatively non-hydrophilic polymers can be treated to increase their hydrophilicity. Such treatment can be carried out either before or after the sintering process. Examples of such treatment include treatment with a surface-active/wetting agent, e.g. Sodium Dodecyl Sulphate (SDS) or more preferably a biocompatible agent such as Crodasinic LS30, (Sodium Lauroyl Sarcosinate) chemical, electrical or radiation treatment, thereby modifying the surface of the material.

To produce such an absorbent material, one or more polymer powders are mixed in a mould. Filling of the mould can be achieved with or without the help of mechanical vibration, this being dependent on the degree of packing required. The mixture is then heated in the mould to a sintering temperature, i.e. one greater than the melting point of the polymer such that the particles of polymer melt and adhere together but not sufficient to flow sufficiently that the porous nature of the material is lost.

The degree of heating above the melting point of the polymer or polymers that can be achieved will depend upon the melt viscosity of the polymer or polymers. If a polymer with a high melt viscosity is chosen then the sintering temperature used can be much higher than the melting temperature. However, if the melt viscosity is low, then the sintering temperature must be very carefully controlled close to the melting point of the polymer.

The mould can be constructed of any suitable material having good thermal conductivity. The mould will be held at the desired temperature until the polymer or polymers have fused satisfactorily. The mould is then cooled and the absorbent material can be removed from the mould.

Suitably, the material can be formed into a pad or swab which would be convenient for obtaining a sample of saliva, for example. The material is easy to handle and works with and lends itself to being formed with a particular configuration.

In a further embodiment apparatus is provided which allows the user to choose different types of collection member which can be attached to the first, "handle" portion.

For example, the apparatus could be provided as a kit, providing the first portion as "standard" as well as a number of different collection members. The different collection members could simply be various comb devices designed to collect different sample volumes. Alternatively, a comb member could be provided and also, for instance, a pad of absorbent material as described herein. The user would then be able to choose the appropriate collection member for the sample to be collected.

The apparatus can be used, therefore, to collect a fixed volume of sample. In the context of the present invention, "fixed" will generally mean a volume falling within a suitable range for use in the test in which the sample volume is to be used. Absolute accuracy will not be required, just sufficient accuracy to ensure that there is sufficient material present for the purposes of any test to be performed on the sample. For example, where a diagnostic test device is to be used, the sample should be sufficient to ensure that the device is not "under" or "over" loaded.

Thus, in the case of a "comb" type device the spaces between the members will define the sample volume and the user simply has to ensure that the spaces between the members are fully occupied with sample. In the case of apparatus incorporating absorbent material it may be useful to include some form of "adequacy" indicator which will allow the user to be certain that a large enough saliva sample, for instance, has been collected. Thus, one could incorporate a food dye, e.g. a blue food dye, in that part of the absorbent material nearest the handle portion of a collector device. Once a liquid sample reaches the dye it will be solubilised and be dispersed (indeed the handle portion could be hollow at least in part to receive the solubilised dye) thus indicating that a sufficient sample has been collected.

The apparatus of the invention can be made of any suitable material, subject of course to the necessity of providing some form of absorbent member, where appropriate. Such materials will include those that can be moulded in the desired configuration. Materials which can be machined or carved to the desired configuration would also be suitable. Examples of such materials would be conventional plastics materials used in this art and known to the skilled man.

As discussed herein the apparatus of the invention will present the sample accurately when interconnected with the device or housing such that the sample will be released or transferred when brought into contact with suitable means. Suitably, therefore, the device or housing incorporating the analyte detection means will include means for transferring the sample to the device or kit. In this way, the fixed sample volume will be released from the apparatus such that the analyte detection process, e.g. diagnostic test, can begin.

In a second aspect, the present invention provides a kit for the detection of an analyte in a sample which comprises:

(i) sample collection apparatus as defined herein; and (ii) means for detecting the analyte.

Suitably, the means for detecting the analyte will comprise:

(i) a reaction area; and (ii) means for transferring the sample to the reaction area.

Suitably, the reaction area is located on a strip of suitable material, e.g. nitrocellulose, nylon or the like. The means for transferring the sample to the reaction area could be a porous or bibulous material such as a filter paper or the like. When the kit is to be used to detect an analyte in a blood sample it will be usual to first separate the red blood cells from the blood plasma since it is often the case that the analyte is present in the plasma only. Thus, the apparatus can further comprise means for separating the blood cells from the blood plasma. This would also be useful in preventing any interference in visualising any colour reaction used to detect the analyte. In one embodiment, the means for transferring the sample to the reaction area also serve to separate the red blood cells from the blood plasma.

In general the reaction area will have fixed thereto one or more agents capable of binding to the analyte. For instance, where the analyte to be detected is an antibody, the reaction area can have fixed thereto one or more binding partners for the antibody, for instance, one or more antigens capable of binding to the antibody. Alternatively, where the analyte to be detected is an antigen, the reaction area can have fixed thereto one or more binding partners for the antigen, e.g. antibodies capable of binding to the antigen.

In a particularly preferred embodiment, the analyte to be detected allows detection of the presence of *H. pylori* i.e. where the analyte is an antigen, it is one derived from *H. pylori,* or when the analyte is an antibody, it is one which binds to at least one antigen derived from *H. pylori.*

Preferably, the apparatus and the analyte detection means will be adapted to interconnect such that, once connected, they cannot be disconnected thus ensuring that no leakage of the sample occurs. In use, therefore, the sample volume will be taken up by the sample collection apparatus. The apparatus will then be interconnected with the analyte detection means. The sample will be presented such that it then passes from the apparatus to the analyte detection means, and thus to the reaction area. Finally, visualisation of the test result will occur.

In other aspects, the present invention provides:

(a) the use of apparatus of the invention in collecting a sample volume, particularly of blood or saliva;

(b) the use of a kit of the invention in detecting an analyte in a sample, particularly in a blood or saliva sample; and (c) a method for detecting an analyte in a sample which comprises the step of collecting a sample volume using apparatus of the invention, preferably provided as part of a kit of the invention. In one embodiment of this aspect the method is used to detect an analyte in a blood or saliva sample, particularly for use in diagnosing *H. pylori* infection.

BRIEF DESCRIPTION OF THE DRAWINGS

Preferred embodiments of the invention will now be described with reference to the accompanying drawings in which.

DETAILED DESCRIPTION OF THE INVENTION

Figure 1:
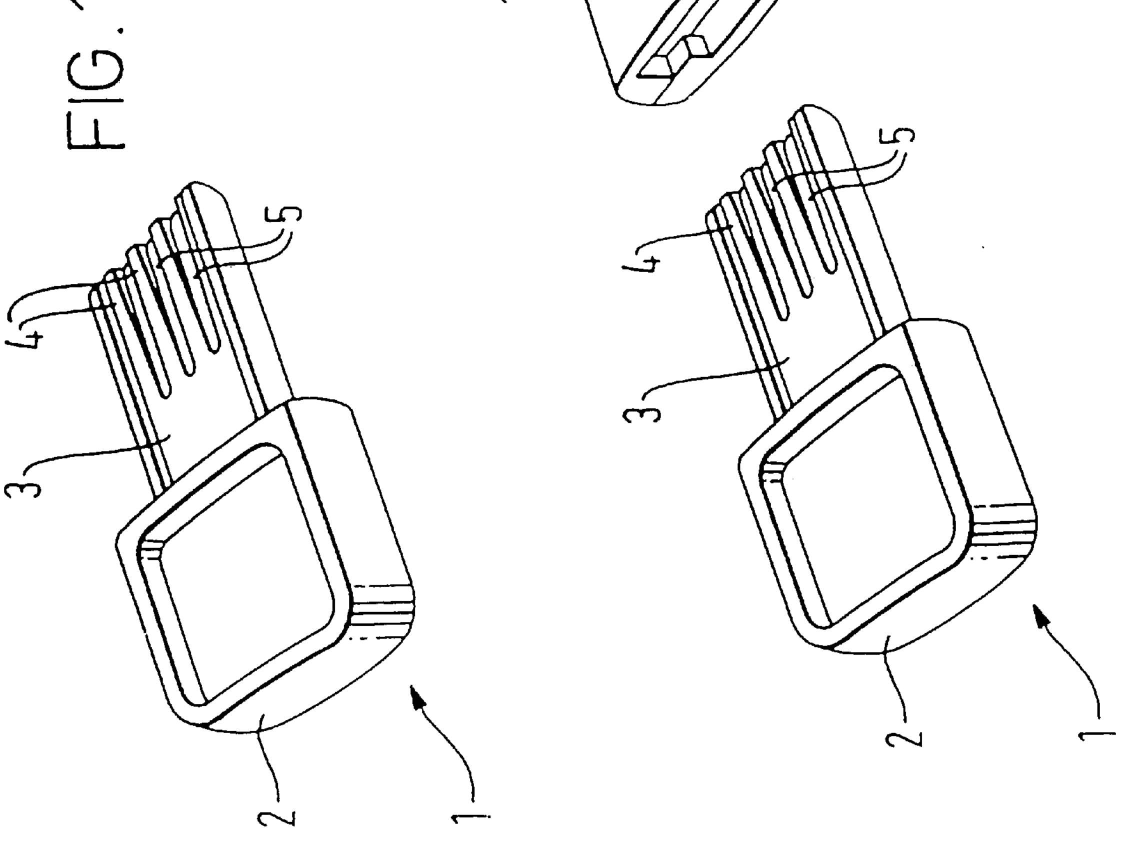
FIG. 1: shows one embodiment of the sample collection apparatus.

FIG. 1 shows one embodiment of the sample collection apparatus of the invention. The apparatus (1) consists of a first portion (2) which is designed to be held by the user, and a second portion (3) which is used for sample collection. Part of the second portion (3) is formed of a number of elongate members (4) which define a series of spaces (5) therebetween. As shown in the figures, elongate members (4) preferably are substantially coplanar. In use, the second portion (3) can be placed in contact with a liquid, e.g. blood. A sample volume of the liquid will flow into the spaces (5) by means of capillary action.

Figure 2:
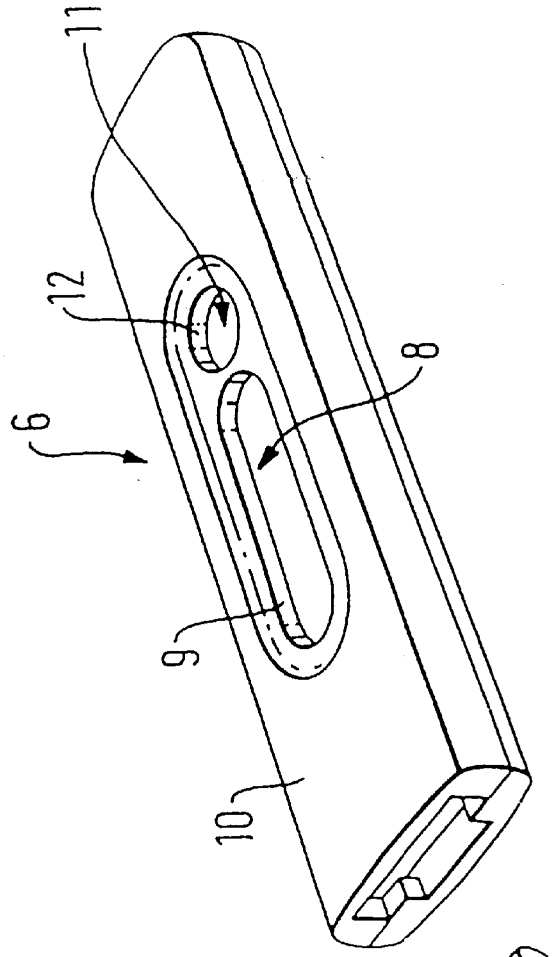
FIG. 2: shows the sample collection apparatus of FIG. 1, together with a form of analyte detection means.

In FIG. 2, the apparatus (1) is shown next to a form of device (6) suitable for detecting an analyte in a sample. It can be seen that the second portion (3) of the sample collection apparatus (1) can be inserted into an opening (7) formed in the device (6). Thus, in use, the collection apparatus (1) carrying the sample can be connected to the device (6) by inserting its second portion (3) into the opening (7). The sample can then be transferred to a nitrocellulose strip (8), at least part of which constitutes the reaction area, which can be seen via a window (9) cut in the upper surface (10) of the device (6). Thus, the result of the test can be visualised via the window (9). The embodiment shown also provides a reference area (11) which can be seen by means of a second window (12) cut in the upper surface (10) of the device (6).

Such a reference area can provide a background to assess the result in the reaction area (8) when visualisation occurs by means of a colour reaction. Alternatively, this area can constitute a "test complete" area. This will allow the user to be sure that sufficient material was loaded for a reliable test result to have been achieved.

Figure 3:
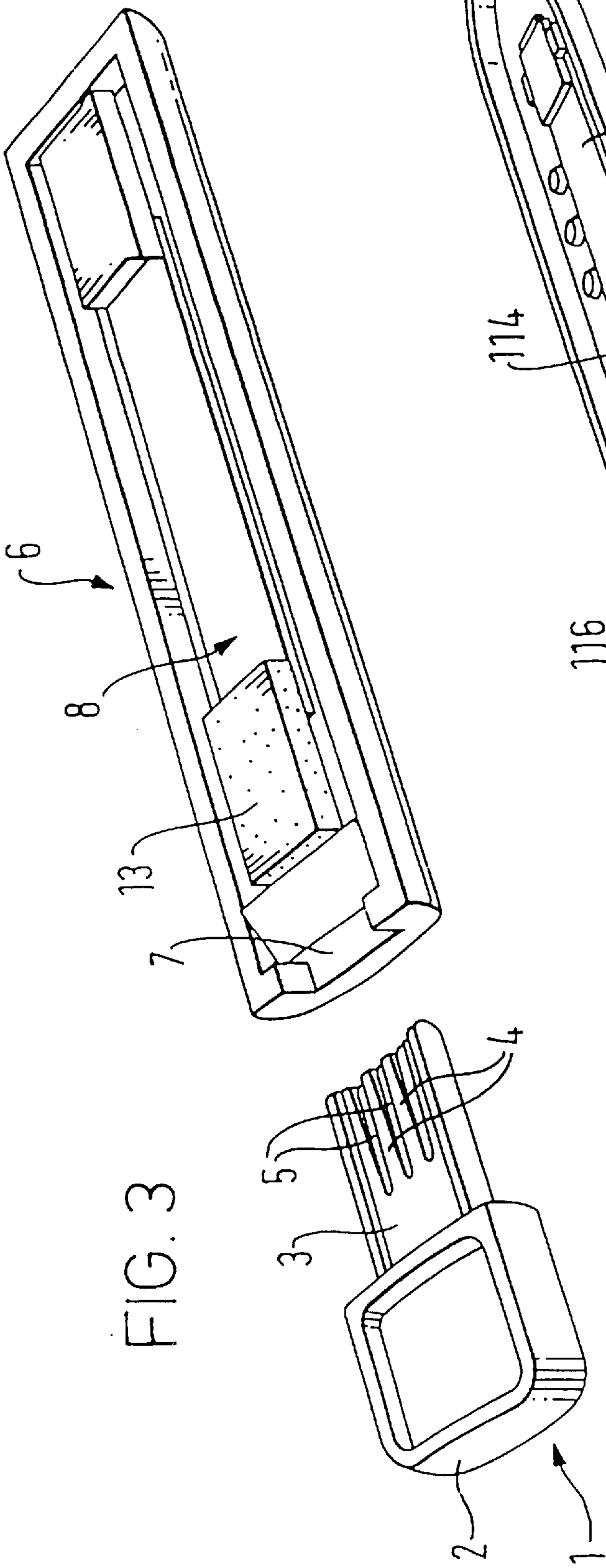
FIG. 3: shows the sample collection apparatus of FIG. 1 together with a sectional view of analyte detection means.

In FIG. 3, the device (6) is shown in longitudinal section, thus showing the internal construction more clearly. In use, the sample collector (1) is attached to the device (6) by inserting its second portion (3) into the opening (7) provided in the device (6). Once inserted, the sample volume held in the spaces (5) between the elongate members (4) contacts a member comprising a porous/bibulous material (13). This member will serve to transfer the sample from the collection apparatus to the nitrocellulose strip (8). In addition, where the sample is a blood sample, it will also serve to separate the blood cells from the blood plasma. The lower surface of the member (13) is in contact with the upper surface of the nitrocellulose strip (8), and so the sample will move generally along and down from the member (13) into the nitrocellulose strip (8) and will be drawn along it.

The whole of the nitrocellulose strip (8) could constitute the reaction area, or, more usually, only a portion will, and fixed to it will be one or more agents capable of binding to the analyte if present in the samples.

For example, in a test for the presence of antibodies to *H. pylori* in a blood sample, at least a portion of the nitrocellulose strip (8) will have fixed to it one or more antigens derived from *H. pylori.* As the sample passes through the strip (8), any *H. pylori* antibodies present in the sample will bind to the fixed antigen(s). The test results can then be read by, for instance, adding to the nitrocellulose strip (8) an agent capable of binding to antibodies generally (for example an anti-IgG antibody) which in turn is bound to a colour reagent, for instance a coloured latex particle. Thus, where the antibodies for the sample have bound to the antigen, a concentration of colour will occur.

A further refinement of the device (6) will be to provide a control area. The control area could be provided adjacent to the reaction area. In this control area can be bound a reference agent. In use, the control area can be designed to bind any colour reagent which passes through the reaction area, but is not bound thereto. In this way, the test can be assessed by the binding of this "excess" reagent to the control area.

This control area thus allows the user to ensure that the test is operating correctly and eliminates false negatives.

Figure 4:
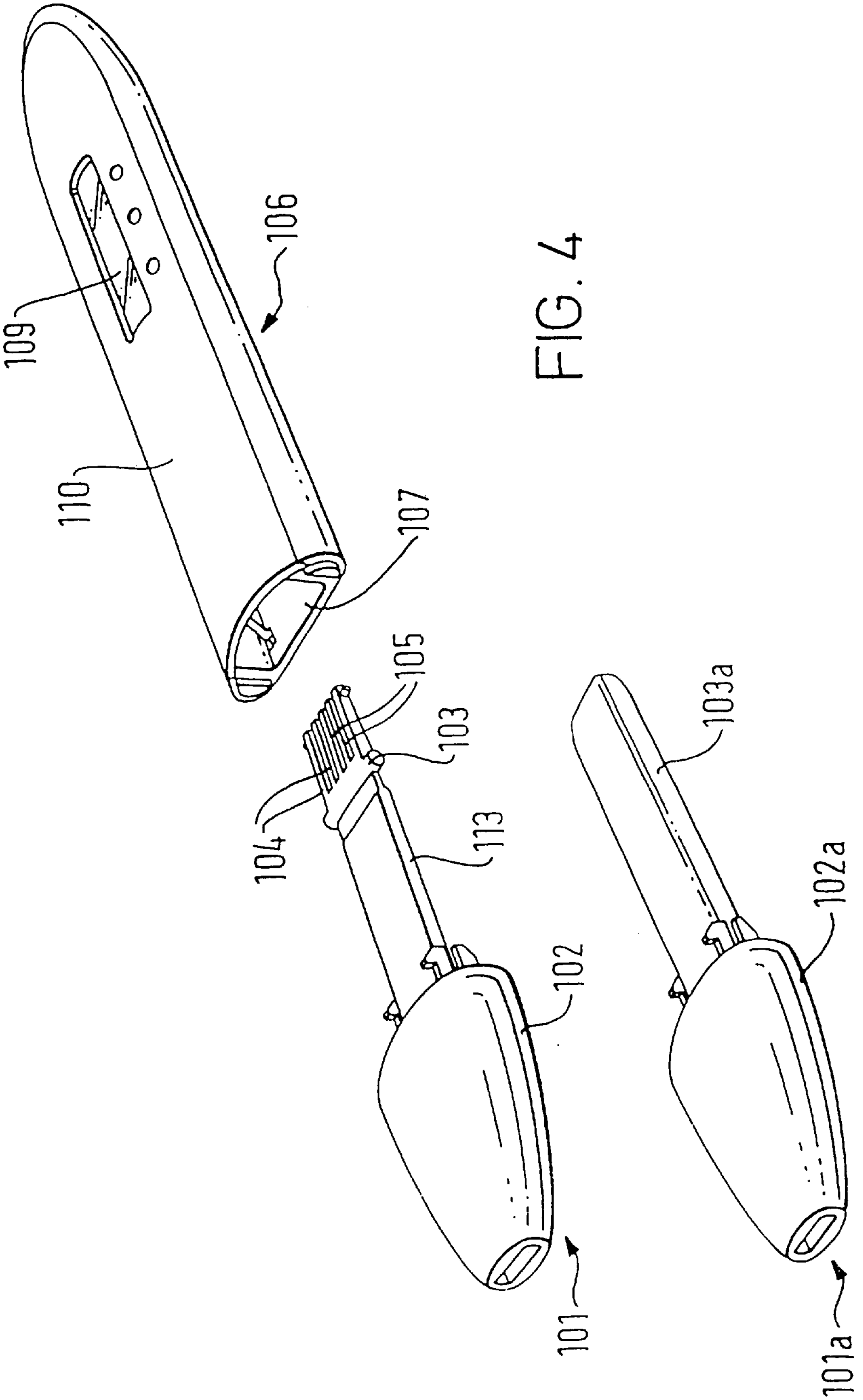
FIG. 4: shows alternative embodiments of the sample collection apparatus showing both a "blood" collector and a "saliva" collector together with an alternative form of analyte detection device.

FIG. 4 shows an alternative embodiment of a "blood" collector (101) as well as a form of collector (101*a*) which comprises a body of absorbent material as described herein. Once again the collector (101/101*a*) has a first portion (102/102*a*) which can be held by the user, and a second portion (103/103*a*) which is used for sample collection. In the case of the "blood" collector (101) there is an elongate member (113) located between the first portion (102) and the collector portion (103). That part of the collector portion (103) which is designed to take up the sample consists of a number of elongate members (104) which define spaces (105) therebetween. Use of such a collector is as described for the collector apparatus described in FIG. 1.

The "saliva" collector (101*a*) is formed from a first portion (102*a*) which is designed to be held by the user, and a second portion (103*a*) formed from a body of absorbent material.

The device (106) suitable for detecting an analyte in the sample is adapted to receive the collector (101/101*a*) via an opening (107). The result of the diagnostic test is read via a window (109) cut in the upper surface (110) of the device (106).

Figure 5:
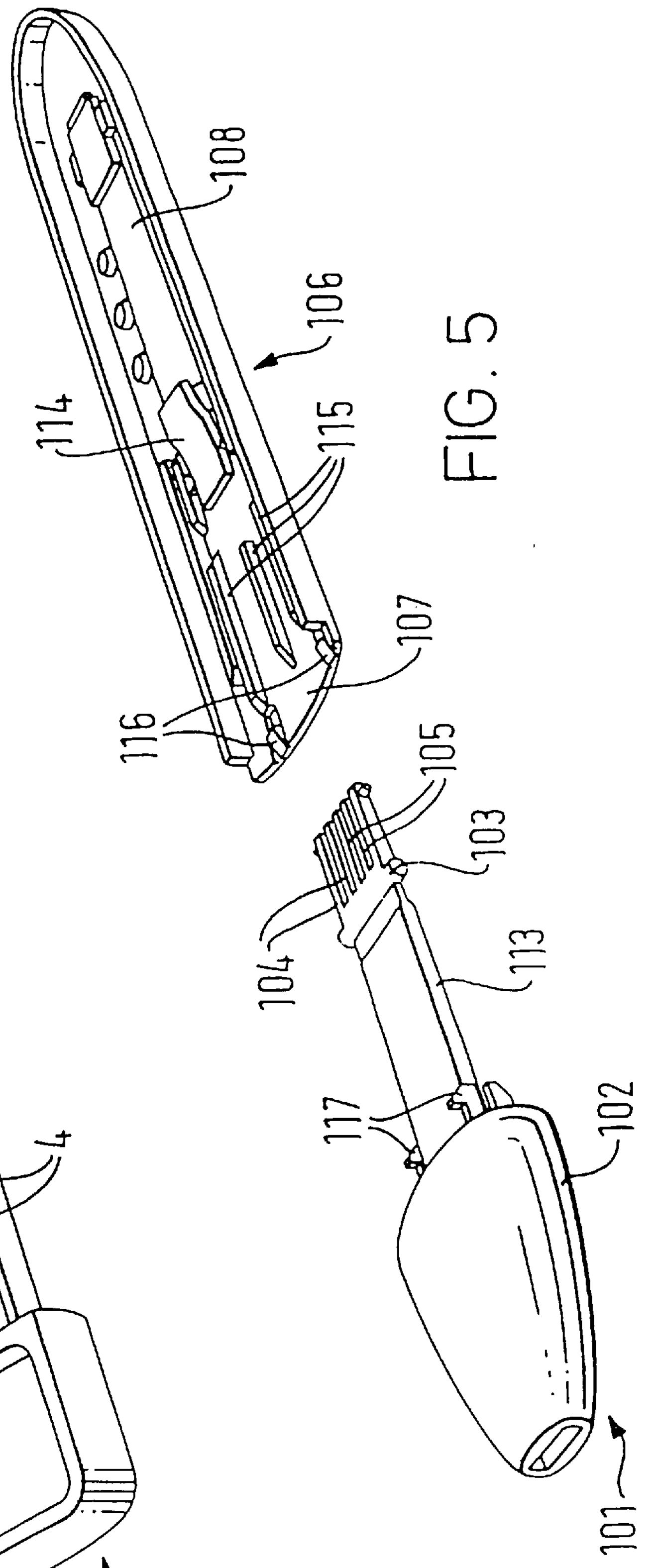
FIG. 5: shows the "blood" collector of FIG. 4 together with a sectional view of an alternative form of analyte detection device.

In FIG. 5 the device (106) is shown in longitudinal section with a "blood" collector (101). The figure shows more clearly how the collector (101) can interact with the device (106) releasing the sample held in the collector portion (103) formed by the elongate members (104). When the collector is inserted into the device (106) via the opening (107) the collector portion (103) and then the elongate member (113) are guided by rails (115). The collector (101) also has engagement means (117) which engage counterpart means (116) which are present in the device (106). These engage and hold the collector (101) in place with the elongate member (113) and collector portion (103) projecting into the interior of the device (106) such that the elongate members (104) are in contact with a bibulous member (114) which in turn is in contact with a nitrocellulose strip (108). Thus, the sample will move through the bibulous member (114), which can also be adapted to separate blood cells from the accompanying plasma, into the nitrocellulose strip (108) where the diagnostic assay commences.

What is claimed is:

1. Sample collection apparatus comprising:

a collector adapted to receive and retain a sample volume of biological fluid, said collector comprising at least two elongate members forming a comb arrangement; and engagement meads configured to engage counterpart means on a device or housing incorporating analyte detection means and a test result visualization area, said engagement means further being configured to hold said sample collection apparatus in place with respect to the device or housing;

wherein upon interconnection with the device or housing at least a part of any sample in said sample collection apparatus will be transferred to the device or housing from said sample collection apparatus for an analyte detection process to be performed within the device or housing and for the process results to be visualized in the test result visualization area.

2. Sample collection apparatus as claimed in claim 1, further comprising a first portion adapted to be held by a user and coupled to said collector.

3. Sample collection apparatus as claimed in claim 2, wherein said collector is detachable from said first portion.

4. Sample collection apparatus as claimed in any one of claims 1 or 3, wherein said engagement means presents said collection apparatus correctly for interconnection with the device or housing for the analyte detection process to begin within the device or housing.

5. Sample collection apparatus as claimed in claim 4, wherein said alignment means also form interconnection means.

6. Sample collection apparatus as claimed in claim 1, wherein said collector is configured to contact, over a substantial proportion of its surface area, means within a device or housing for transferring the sample from said collector to the device or housing.

7. Sample collection apparatus as claimed in claim 1, wherein a fixed sample volume is taken up by said collector by capillary action.

8. Sample collection apparatus as claimed in claim 1, wherein said elongate members are formed by plates.

9. Sample collection apparatus as claimed in claim 1, wherein said comb is formed from four, five or six elongate members, providing three, four or five spaces therebetween, respectively, to receive the sample volume.

10. Sample collection apparatus as claimed in claim 1, wherein said collector comprises a two-dimensional array of members with spaces formed therebetween.

11. Sample collection apparatus as claimed in claim 1, wherein said collector comprises absorbent material formed into a pad.

12. Sample collection apparatus as claimed in claim 11, wherein said absorbent material has been treated to increase its hydrophilicity.

13. Sample collection apparatus as claimed in claim 12, wherein the treatment involves treatment with a wetting agent such as SDS or Sodium Lauroyl Sarcosinate.

14. Sample collection apparatus as claimed in claim 1, wherein said collection apparatus is shaped to interlock with a device or housing incorporating an analyte detection means such that once connected with the device incorporating the analyte detection means said apparatus cannot be disconnected therefrom.

15. Sample collection apparatus comprising at least two substantially coplanar elongate members spaced apart to receive a sample volume of biological fluid therebetween upon bringing said at least two members into contact with a biological fluid.

16. Sample collection apparatus as claimed in claim 15, wherein a fixed sample volume is taken up between said elongate members by capillary action.

17. Sample collection apparatus as claimed in claim 15 or claim 16, further comprising a first portion adapted to be held by the user and coupled to said elongate members.

18. Sample collection apparatus as claimed in claim 15, wherein said elongate members are formed by plates.

19. Sample collection apparatus as claimed in claim 18, wherein said elongate members form a comb arrangement.

20. Sample collection apparatus as claimed in claim 19, wherein said comb is formed from four, five or six elongate members, providing three, four or five spaces therebetween, respectively, to receive the sample.

21. Sample collection apparatus as claimed in claim 15, wherein said elongate members form a two-dimensional array of members with spaces formed therebetween.

22. Sample collection apparatus as claimed in claim 15, wherein said sample collection apparatus is configured to be brought into contact with an analyte detection means.

23. Sample collection apparatus as claimed in claim 22, wherein said sample collection apparatus is configured such that once connected with a device incorporating the analyte detection means said sample collection apparatus cannot be disconnected therefrom.

24. Sample collection apparatus adapted to interconnect with a device or housing which incorporates analyte detection means, said sample collection apparatus comprising absorbent material treated with a wetting agent selected from the group consisting of Sodium Dodecyl Sulphate and Sodium Lauroyl Sarcosinate to increase its hydrophilicity, wherein upon interconnection with the device or housing at least a part of any sample in said sample collection apparatus will be transferred to the device or housing from said sample collection apparatus.

25. Sample collection apparatus as claimed in claim 24, wherein said absorbent material is formed into a pad.

26. Sample collection apparatus as claimed in claim 24, wherein said pad is formed from sintered polymer powders.

* * * * *